US008545522B2

(12) United States Patent
Shpaichler et al.

(10) Patent No.: US 8,545,522 B2
(45) Date of Patent: Oct. 1, 2013

(54) DEVICE FOR WOUND SUTURING AND HEMOSTASIS IN THE THORACIC AND THE ABDOMINAL WALL MAINLY IN ENDOSCOPIC OPERATIONS

(76) Inventors: Vladimir Shpaichler, Jerusalem (IL); Evgeny Shpaichler, Jerusalem (IL)

( * ) Notice: Subject to any disclaimer, the term of this patent is extended or adjusted under 35 U.S.C. 154(b) by 0 days.

(21) Appl. No.: 13/532,021

(22) Filed: Jun. 25, 2012

(65) Prior Publication Data

US 2012/0265223 A1      Oct. 18, 2012

Related U.S. Application Data

(63) Continuation-in-part of application No. 11/975,219, filed on Oct. 18, 2007, now abandoned, which is a continuation-in-part of application No. PCT/IL2006/000433, filed on Apr. 6, 2006.

(30) Foreign Application Priority Data

Apr. 19, 2005   (IL) .......................................... 168129

(51) Int. Cl.
*A61B 17/04*    (2006.01)
*A61B 17/06*    (2006.01)

(52) U.S. Cl.
USPC .......................................... 606/148; 606/139

(58) Field of Classification Search
USPC ......... 606/139, 144, 148, 213, 228; 600/203, 600/205, 208, 114
See application file for complete search history.

(56) References Cited

U.S. PATENT DOCUMENTS

| 4,553,543 | A | * | 11/1985 | Amarasinghe ................ 606/148 |
| 5,496,335 | A | | 3/1996 | Thomason et al. |
| 5,507,758 | A | | 4/1996 | Thomason et al. |
| 5,562,688 | A | * | 10/1996 | Riza .............................. 606/148 |
| 5,716,369 | A | | 2/1998 | Riza |
| 5,830,232 | A | | 11/1998 | Hasson |

(Continued)

FOREIGN PATENT DOCUMENTS

WO     WO 2011/128392     * 10/2011

OTHER PUBLICATIONS

International Search Report for PCT/IL06-00433 dated Jul. 20, 2007.

(Continued)

*Primary Examiner* — Darwin Erezo
*Assistant Examiner* — Jing Ou
(74) *Attorney, Agent, or Firm* — Fleit Gibbons Gutman Bongini & Bianco PL; Paul D. Bianco; Martin Fleit (57) ABSTRACT

A device for use with a trocar in suturing trocar wounds with flexible needles. The device includes a ring encompassing the trocar positionable adjacent to a body wall. The ring, often a split ring, has a pair of guide channels passing through it, each channel including an entry hole and an exit hole. These guide holes are disposed symmetrically on the ring such that the two entry holes and the two exit holes form lines passing through the longitudinal axis of the trocar. The channels are curved near their respective entry holes. The guide channels are angled in the region of the exit holes so that when the needles exit the channels into the body wall and then the body cavity they are at a predetermined distance from the nearest point on the trocar. The above described device forms a suturing system with the trocar.

11 Claims, 10 Drawing Sheets

(56) References Cited

U.S. PATENT DOCUMENTS

| | | | |
|---|---|---|---|
| 6,183,485 B1* | 2/2001 | Thomason et al. | 606/148 |
| 6,383,208 B1* | 5/2002 | Sancoff et al. | 606/213 |
| 6,743,242 B2 | 6/2004 | Guo | |
| 7,390,328 B2* | 6/2008 | Modesitt | 606/144 |
| 7,402,166 B2* | 7/2008 | Feigl | 606/144 |
| 7,850,701 B2* | 12/2010 | Modesitt et al. | 606/144 |
| 7,951,117 B2* | 5/2011 | Wingardner et al. | 604/164.09 |
| 2006/0030868 A1 | 2/2006 | Bennett, III | |
| 2010/0069930 A1* | 3/2010 | Roslin et al. | 606/151 |
| 2011/0270282 A1* | 11/2011 | Lemke | 606/148 |
| 2012/0245536 A1* | 9/2012 | Gerber et al. | 604/288.02 |

OTHER PUBLICATIONS

For U.S. Appl. No. 11/975,219: Office actions dated Mar. 14, 2012, Jul. 19, 2011 Response dated Oct. 19, 2011.

Z. Shaher, "Post Closure Techniques", Surgical Endoscopy, 2007, 21:1264-74.

* cited by examiner

DEVICE FOR WOUND SUTURING AND HEMOSTASIS IN THE THORACIC AND THE ABDOMINAL WALL MAINLY IN ENDOSCOPIC OPERATIONS

CROSS REFERENCE TO RELATED APPLICATION

This application is a continuation-in-part application of U.S. application Ser. No. 11/975,219, filed Oct. 18, 2007, which itself is a continuation-in-part application of PCT Appl. No. PCT/IL2006/000433 (Int. Publ. No. WO 2006/111955) filed Apr. 6, 2006, titled "Device for Wound Suturing and Hemostasis in the Thoracic and the Abdominal Wall Mainly in Endoscopic Operations". The aforementioned PCT application claimed priority from Israel Pat. App. 168129, filed Apr. 19, 2005.

FIELD OF THE INVENTION

The present invention relates to the field of medicine and veterinary medicine and, more particularly, to devices for wound suturing and hemostasis in endoscopic, mainly, laparoscopic and thoracoscopic, operations. The invention may also be used for suturing wounds of any etiology similar to those formed during the endoscopic operations.

STATE OF THE ART

As it is known, an endoscopic operation comprises the following steps:
- insertion of a port through the abdominal or the thoracic wall, into the abdominal or the thoracic cavity, respectively, with the resultant formation of a wound and wound channel,
- introduction of a surgical or a diagnostic instrument into the abdominal or the thoracic cavity through the port channel,
- performing the operation or the diagnostic procedure with the help of the instrument,
- removing the instrument,
- removing the port,
- suturing the wound in the abdominal or the thoracic wall.

It should be mentioned that once the port is removed the wound becomes an unstable layer structure and the wound channel changes its shape.

At present, two methods of wound suturing upon the removal of the port are known.

According to one of them, the wound is sutured manually with the help of surgical thread-guiding members, for example clamp needles, and without any special devices. This method is highly traumatizing and labor-consuming as the selection of the right directions of the thread-guiding members inserted through the abdominal or the thoracic wall into the pre-specified points of the body requires quite a considerable amount of time.

Moreover, upon the removal of the port the wound becomes an unstable layer structure. Substantial disarrangement of approximation of the layers of the abdominal or the thoracic wall takes place during the wound suturing. The disarrangement of approximation is also contributed to by the circumstance that a strictly directed suture as required by surgical standards is impossible to achieve manually. In its turn, the disarrangement of approximation leads to formation of inter-tissue cavities causing various post-surgery complications such as bleeding, suppuration, and hernias.

The other method involves the use of special devices which diminish the traumatizing effect of wound suturing and the amount of labor required.

In practice, a device used until recently for wound suturing in laparoscopic operations comprised of a tubular body with a suturing unit built therein. It included two needles with threads positioned parallel to the longitudinal axis of the tubular body. When such device is inserted into a body cavity and the suturing unit is advanced out of the tubular body the needles move apart. The tubular body together with the suturing unit is then drawn upwards and the abdominal wall is pierced by the parallel needles. To remove the device from the abdominal cavity, the tubular body is inserted into the cavity again and the suturing unit is returned into the tubular body. The use of this device reduces the traumatizing effect of suturing but layer approximation remains significantly disarranged because of the parallel motion of the threads through the thick sutured tissue.

Another device for wound suturing in laparoscopic operations is known (Catalogue of "Inlet Medical, Inc.", 2002, Carter—Thomason Instruments, Art. No CTI-SE). The device comprises a cone-shaped member having a pair of guides for two thread-grasping members, or graspers, functioning jointly during the wound suturing. The guides are oriented in such a manner that when the cone-shaped member is in the wound channel they determine the trajectories of motion of the thread-grasping members. The thread-grasping members are inserted through the abdominal wall into zones containing preset points.

The cone-shaped member is inserted with its apex into the wound channel when the port is removed. The graspers are then inserted into the preset points through the guides in the cone-shaped member.

The use of this device reduces the traumatizing effect during wound suturing but even in this case the wound remains an unstable layer structure, and the approximation of layers of the abdominal wall is disarranged during wound suturing, as described above. This is accounted for, primarily, by the circumstance that the wound surface only partially contacts that of the cone-shaped member.

Besides, after the port is removed, the search for the wound channel with the cone apex is often difficult and may cause a change in the wound configuration and a further disarrangement of its layer structure.

Finally, the necessity of searching for the wound channel while using the above devices makes wound suturing after an operation much more difficult.

SUMMARY OF THE INVENTION

The object of the present invention is, therefore, the task of developing a device for wound suturing and hemostasis in endoscopic operations that would allow to preserve the initial shape of the wound channel and the stable layer structure of the wound at the moment of suturing thereby diminishing the probability of post-surgery complications. The object of the present invention is further to provide a device that will ensure the initially correct directions of motion of thread-guiding members inserted through the abdominal or the thoracic wall into pre-specified points of the body thereby diminishing the traumatizing effect of wound suturing and reducing labor and time expenditures connected with suturing.

The device of the present invention comprises a body having a tubular wall with an outer cross-sectional perimeter matching the cross-sectional perimeter of a pre-specified wound channel. The length of the tubular wall exceeds the preset length of the wound channel. There is at least one pair of guides on the body for two thread-guiding members. Without intending to limit the nature of these members, these members may be needles. These thread guiding members function jointly during wound suturing and hemostasis. The guides are fixed on the body and oriented so as to ensure that the trajectories of motion of the thread-guiding members that guide the threads are lead into the pre-specified points of the body through the abdominal or the thoracic wall.

In another aspect of the present invention, there is provided a device for use with a trocar in suturing trocar wounds using flexible needles. The trocar has a longitudinal axis and may extend through a trocar wound in a body wall and into a body cavity. The device includes a ring encompassing the trocar. The ring is movably positionable so as to be positioned adjacent to the body wall. The ring has a pair of guide channels passing through it for guiding the needles through the body wall into the body cavity. Each channel includes an entry hole and an exit hole. The entry and exit holes are disposed symmetrically on diameters of the ring. The two entry holes form a line passing through the longitudinal axis of the trocar on one diameter of the ring and the two exit holes form a second line passing through the longitudinal axis of the trocar on a second diameter of the ring. The channels are smoothly curved near their respective entry holes; the smooth curves join the straight portions of their respective channels. The straight portions of the channels extend away from the curves toward the exit holes and constitute about 50-80% of the total length of the channels.

In the device, the curved portion of the channels has a curvature that allows an angle of entry of the needles into the entry holes at an angle of less than 30 degrees.

In the device, the guide channels are angled at a predetermined angle in the region of their respective exit holes so that the flexible needles passing through the channels exit from the exit holes along an exit axis into the body wall and then the body cavity. This results in the needles being at a predetermined distance of between 1 and 2.5 cm from the nearest point on the trocar when the needles enter the body cavity. The needles as they enter the body cavity are symmetrically disposed with respect to the longitudinal axis.

The channels are typically sized to have a diameter only slightly larger than the diameter of the flexible needles passing through the channels.

The pair of channels are angled away from each other when proceeding from their respective entry holes toward their respective exit holes.

In yet another embodiment of the device, the ring is a split ring having a closed configuration and an open configuration, each half of the split ring has an entry hole, an exit hole and a guide channel. The entry holes are disposed symmetrically on a diameter of the split ring forming a line passing through the longitudinal axis of the trocar and the exit holes are disposed symmetrically on a second diameter of the split ring forming a second line passing through the longitudinal axis of the trocar when the split ring is in both its closed or open configurations. Each half of the split ring is in mechanical connection with a spring member that is operable to cause the halves of the split ring to transition from their open to their closed configuration and vice versa. The channels are smoothly curved near their respective entry holes, the smooth curves joining the straight portions of their respective channels. The straight portions extend from the curves to the exit holes of the channels and constitute about 50-80% of the length of the channels.

In this latter embodiment, the curved portions of the channels have a curvature that allows an angle of entry of the needles into the entry holes at an angle of less than 30 degrees.

Also in this latter embodiment, the guide channels are typically angled at a predetermined angle in the region of their exit holes so that the flexible needles pass through the channels and exit from them into the body wall and then the body cavity along an exit axis of the channels. When the needles enter the body cavity they are at a predetermined distance of between 1 and 2.5 cm from the nearest point on the trocar. The needles are symmetrically disposed with respect to the longitudinal axis of the trocar.

Further in this latter embodiment, the pair of channels are angled away from each other when proceeding from their respective entry holes toward their respective exit holes.

Also in this latter embodiment, the channels are sized to have a diameter only slightly larger than the diameter of the flexible needles to be passed through the channels.

In yet another aspect of the invention there is provided a system for suturing trocar wounds which extend through a body wall to a body cavity. The suturing is effected with flexible needles. The system includes a trocar having a mechanically connected head and body and having a longitudinal axis extending through the trocar body. The trocar is positionable to extend through the body wall into the body cavity by way of the trocar wound. The system further includes a ring encompassing the trocar. The ring is movably positionable to be positioned adjacent to the body wall. The ring has a pair of guide channels passing through it for guiding the needles through the body wall into the body cavity. Each channel includes an entry hole and an exit hole. The entry holes are disposed symmetrically on a diameter of the ring such that the two entry holes form a line passing through the longitudinal axis of the trocar. The two exit holes are disposed symmetrically on a diameter of the ring such that the two entry holes form a second line passing through the longitudinal axis of the trocar. The channels are smoothly curved near their respective entry holes. The smooth curves join the straight portion of their respective channels. The straight portion extends from the curves to the exit holes of the channels and constitutes about 50-80% of the length of the channels.

In the system, the curved portion of the channels has a curvature that allows an angle of entry of the needles into the entry holes at an angle of less than 30 degrees.

In the system, the guide channels are angled at a predetermined angle in the region of the exit holes so that the flexible needles passing through the channels exit from them into the body wall and then the body cavity along an exit axis of the channels. When the needles enter the body cavity they are at a predetermined distance of between 1 and 2.5 cm from the nearest point on the trocar body. The needles are symmetrically disposed with respect to the longitudinal axis.

In the system, the channels are sized to have a diameter only slightly larger than the diameter of the flexible needles to be passed through the channels.

Also in the system, the pair of channels are angled away from each other when proceeding from their respective entry holes toward their respective exit holes.

Further in the system, the ring is a split ring having a closed configuration and an open configuration. Each half of the split ring has an entry hole, an exit hole and a guide channel. The entry holes are disposed symmetrically on a diameter of the split ring forming a line passing through the longitudinal axis of the trocar. The exit holes are also disposed symmetrically on another diameter of the split ring and they form a second line passing through the longitudinal axis of the trocar when the split ring is in both its closed and open configurations. Each half of the split spring is in mechanical connection with a spring member that is operable to cause the halves of the split ring to transition from its open to its closed configuration and vice versa. The channels are smoothly curved near their respective entry holes. The smooth curves join with the straight portions of their channels. The straight portions extend from the curves to the exit holes of the channels and constitute about 50-80% of the length of the channels.

In the system with the split ring, the curved portion of the channels have a curvature that allows an angle of entry of the needles into the entry holes at an angle of less than 30 degrees.

Also in the system with the split ring, the guide channels are angled at a predetermined angle in the region of the exit holes so that the flexible needles passing through the channels exit from them into the body wall and then the body cavity along an exit axis of the channels. The needles are at a predetermined distance of between 1 and 2.5 cm from the nearest point on the trocar body when the needles enter the body cavity. The needles are symmetrically disposed with respect to the longitudinal axis.

Further in the system with the split ring, the pair of channels are angled away from each other when proceeding from their respective entry holes toward their respective exit holes.

Also further in the system with the split ring, the channels are sized to have a diameter only slightly larger than the diameter of the flexible needles to be passed through the channels.

The present invention will be understood more fully from the detailed description given herein below and from the accompanying drawings of the preferred embodiment of the invention which, however, should not be construed as exhaustive to the invention but are for explanation and understanding only.

DETAILED DESCRIPTION OF THE PREFERRED EMBODIMENTS OF THE INVENTION

Figure 1:
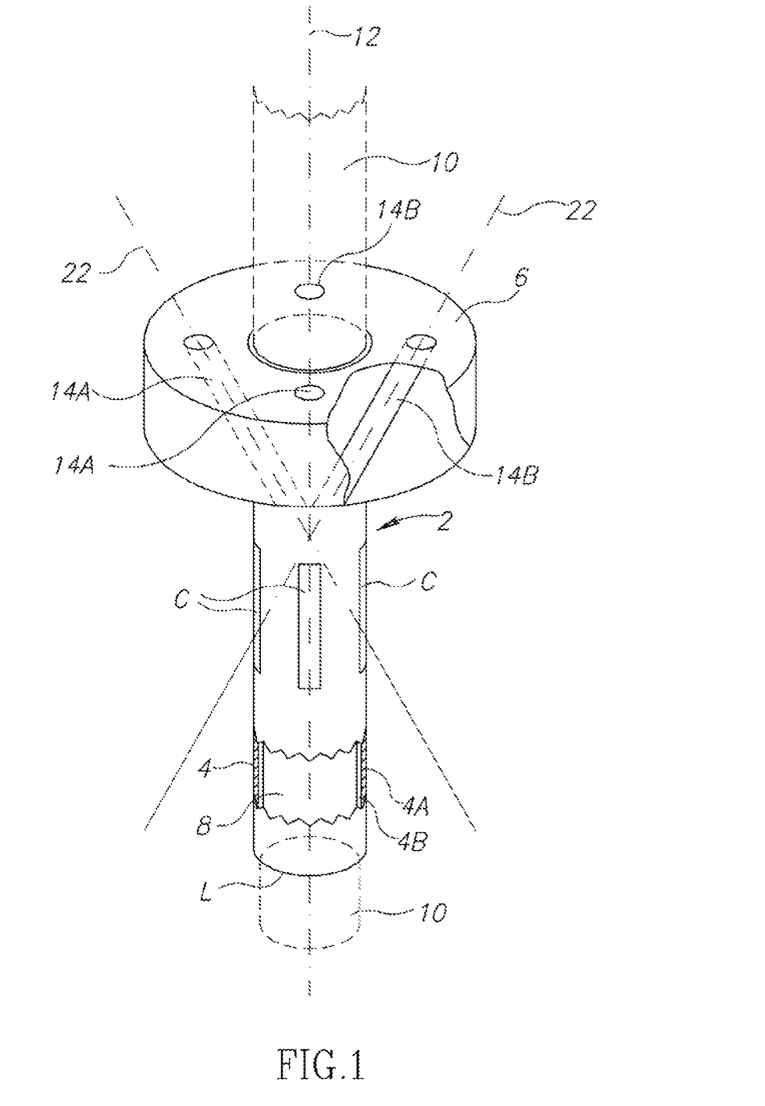
FIG. 1 shows a general view of the device of the present invention.

The proposed device for wound suturing and hemostasis is used after endoscopic operations wherein a port, also at times referred to herein as an endoscopic access port, is employed. The device (FIG. 1) comprises body 2 having a cylindrical tubular wall 4 equipped with a cap 6 on one end thereof. Tubular wall 4 is intended to preserve the initial shape of wound channel 8 (FIGS. 2,3) during the entire operation. Embodiments of the present invention are possible wherein the tubular wall has other than a cylindrical shape. Outer side 4a of wall 4 in its shape and size (length "L" of the outer cross-sectional perimeter of outer side 4a of wall 4) matches the preset shape and size of wound channel 8. The term "size of wound channel" denotes the cross-sectional perimeter of the wound channel wall. "Size matching" means the equivalence of sizes with acceptable deviations small enough to allow the fulfillment of the object of the present invention. Matching is easy to determine experimentally. In another embodiment, the cross-sectional shape of our device may be different from the cross-sectional shape of the wound channel. For example it may be star-shaped. In such a case the shape of the body wall will be chosen in order to preserve the stable layer structure of the wound Inner side 4b of wall 4 has a diameter making it possible for port 10 to be moved inside wall 4 along its longitudinal axis 12. In cap 6, there is provided paired guides 14a and 14b formed in the shape of slots. These guides are intended to guide thread-guiding members 16, the latter typically, but without intending to limit the invention, being needles. Guides 14a, 14b of each pair are positioned symmetrically relative to axis 12. Guides 14a, 14b are oriented so that when port 10 is in its operating position they ensure such trajectories of motion of thread-guiding members 16 (FIG. 2, 4) that the threads guided by them are lead into pre-specified points "a" and "b" in abdominal or thoracic cavity 18 through abdominal or thoracic wall 20, respectively. By "operating position" of the port such position is meant whereby tubular wall 4 is inserted into the wound channel throughout the length of the latter. The number of guides 14a, 14b and their orientation are determined by the specific purpose of the device (wound suturing, hemostasis or both). The areas of tubular wall 4 located in zone "c" of trajectories 22 of motion of thread-guiding members 16 are made of a material that may be pierced through by thread-guiding members 16, for example, of silicon. Such an arrangement does not require modification of the design of existing ports.

The proposed device is operated as follows.

Before the beginning of an endoscopic operation the port 10 is inserted into tubular wall 4 of body 2 and is fixed therein by any of several known methods, for example, by means of a threaded connection (not shown for considerations of simplicity). Tubular wall 4 together with port 10 is then inserted through abdominal or thoracic wall 20 into abdominal or thoracic cavity 18, respectively. Thereby a wound—wound channel 8—is formed in abdominal or thoracic wall 20. After that, a surgical or a diagnostic instrument (not shown) is inserted into abdominal or thoracic cavity 18 through the inner cavity of port 10, a surgical or a diagnostic manipulation is performed, and the instrument is removed. Then port 10 is detached from body 2 and removed therefrom whereas tubular wall 4 stays in wound channel 8 providing for a reliable preservation of the initial shape of wound channel 8 and for the stability of the wound layer structure.

Another embodiment of the present invention is possible wherein the device is used separately from the port. In this case the port is inserted into abdominal or thoracic cavity 18 without the proposed device. Before the expected removal of the port from the wound channel a guide (not shown) is passed through the port whereupon the latter is removed. The guide staying in the wound channel makes it possible to preserve the stable layer structure of the wound. The device of the present invention is then inserted into the wound along the guide. This arrangement, too, does not involve the modification of the design of existing ports, and, moreover, it is more universal as it allows the same device to be employed in different wound channels with comparable cross-sectional sizes.

Wound suturing with the help of the proposed device is performed as follows.

First thread-guiding member 16 together with (suturing) thread 24 is moved along guide 14a ensuring trajectory 22, to be inserted into preset point "a" of abdominal or thoracic cavity 18, and successively pierces through zone "c" of tubular wall 4, and abdominal or thoracic wall 20. Along guide 14b, second thread-guiding member 16 with graspers (not shown) is inserted into point "b" in a similar manner, the graspers grasping thread 24 to guide it out of the abdominal or thoracic cavity along the same trajectory. Then the device for wound suturing is removed from wound channel 8 and thread 24 is tied forming a suture. A second suture may be made with the help of a second pair of guides 14, when necessary.

Depending on the purpose of suturing (tightening the wound, suppressing bleeding in the wound area, fixing the tissues in the wound area), the suture may cut the central axis of the wound channel or lie beyond it.

Figure 2:
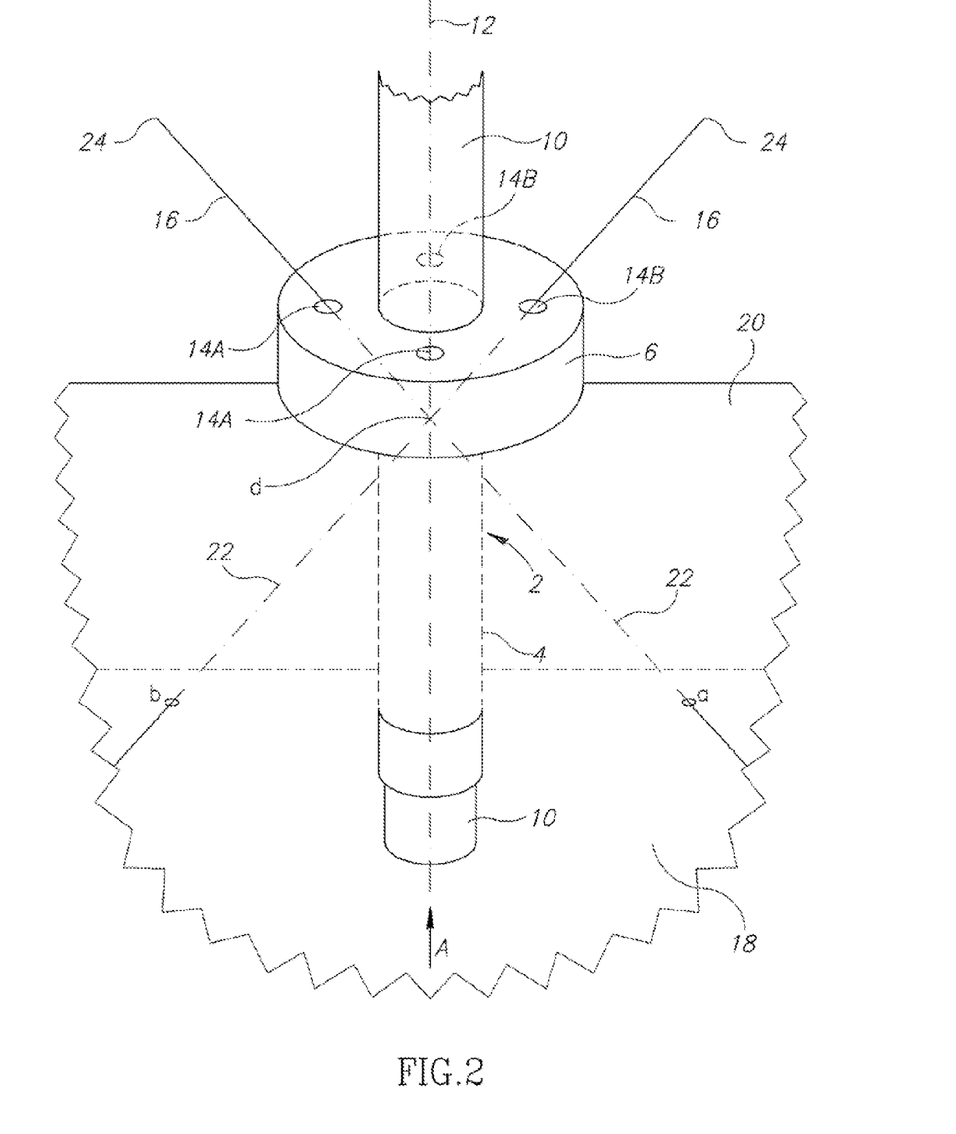
FIG. 2 shows a general view of the device in FIG. 1 in its operating position.
Figure 3:
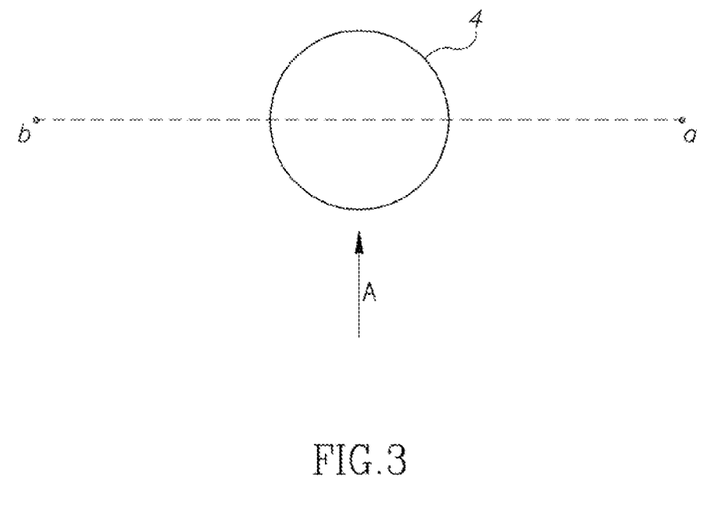
FIG. 3 is a view along arrow A in FIG. 2.

In the former instance, guides 14 are oriented so that point "d" of intersection of trajectories 22 lies on longitudinal axis 12 (FIG. 2, 3). Such positioning of the suture is optimal for tightening the wound itself.

Figure 4:
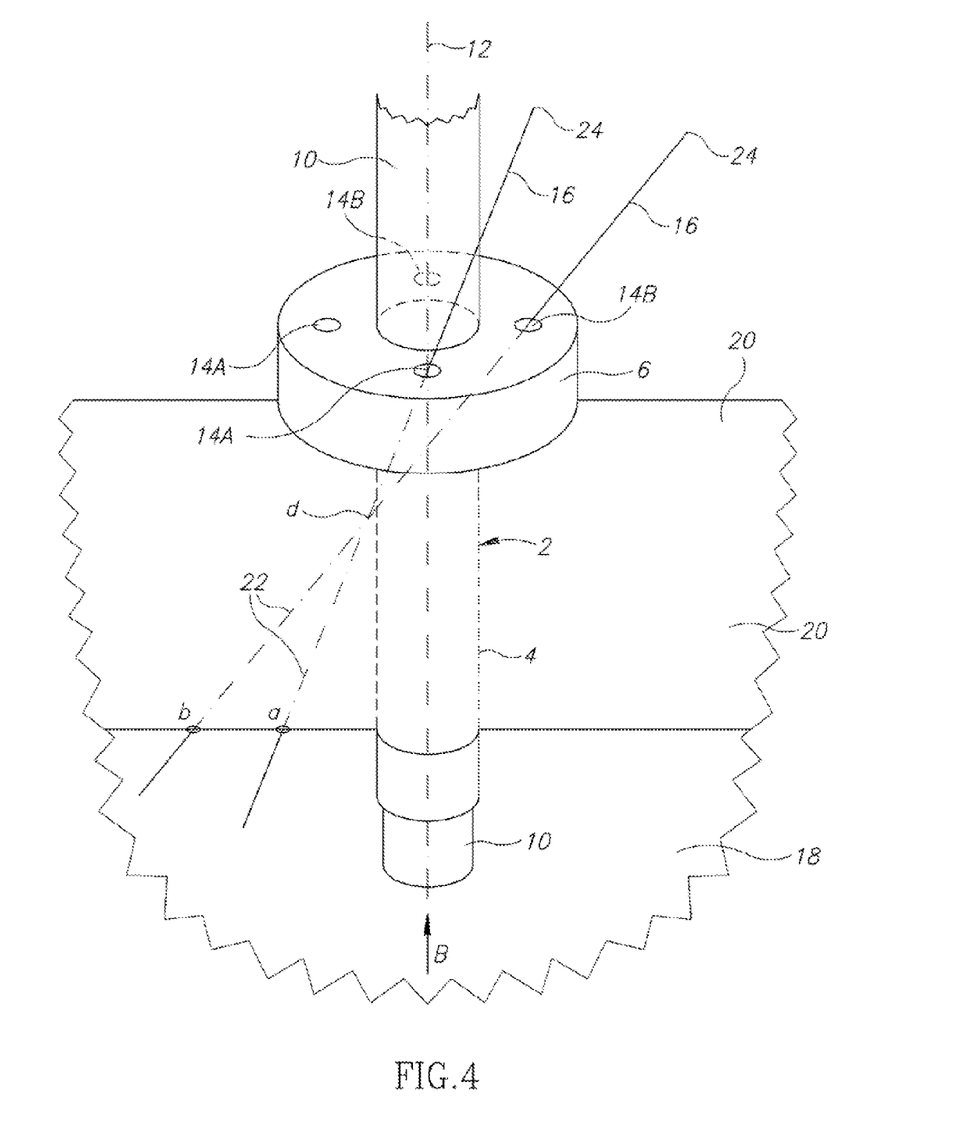
FIG. 4 shows a general view of the device of the present invention in its operating position used for another purpose.
Figure 5:
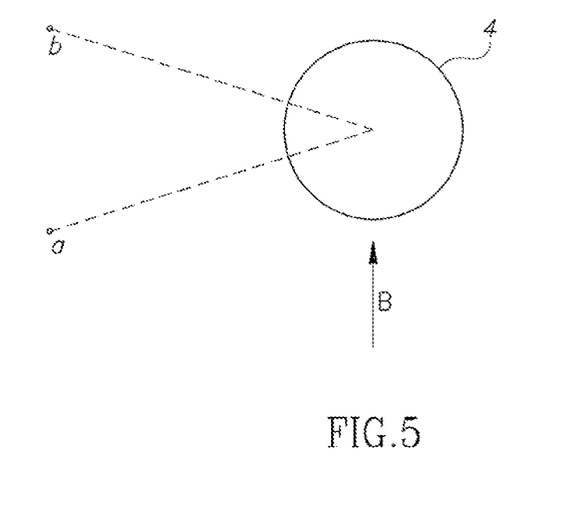
FIG. 5 is a view along arrow B in FIG. 4.

In the latter instance, guides 14 are oriented so that point "d" of intersection of trajectories 22 lies beyond longitudinal axis 12 (FIG. 4, 5). Such suture is used, for example, to suppress marginal bleeding.

In one of the embodiments of the present invention (not shown in the figures), port 10 itself may be used in the capacity of the body, or its part, of the proposed device. In this case, port 10 itself, or the mentioned additional part of the body, has guides 14 and the zones "c" may be made of a material to be pierced through by thread-guiding members 16. This arrangement, however, may require modifications to the design of the port.

In this arrangement, when the surgical or the diagnostic instrument is removed from cavity 18, port 10 stays in wound channel 8 preserving the initial shape of wound channel 8 and the stable layer structure of the wound. Suturing is performed as described above.

In embodiments where port 10 itself, or one of its parts, functions as body 2 (or part thereof) of the device of the present invention as discussed above, particularly when it serves as the tubular-shaped wall portion of body 2, guides 14 may be positioned in body 2 and oriented by any of many different ways.

The guides may be positioned in a guide containing member (not shown) which may be fixably or removably attached to the port. The guides are fixably oriented within the guide containing member. Without intending to limit the form and types of guide containing members, cap 6 of FIG. 1 may be considered to be an example of a guide containing member.

The guide containing member (not shown) may be made of a plastic or polymeric material integrally molded to the access port, the latter typically made of plastic. Alternatively, the guide containing member may be made from a separate piece fixed to the port by any of many different types of attachment means known to those skilled in the art, such as screws, clips, or elastic means. These attachments are exemplary only and are not intended to be limiting. When the guide containing member is attached to the tubular-shaped wall structure of the port, it may be attached either entirely around the tubular-shaped wall structure of the port or only on one side of the port's wall structure.

When screws, clips, elastomeric means, etc. are used to join a guide containing member to the body, the separate guide containing member may function as a universal guide containing member irrespective of the diameters and/or dimensions of the port's tubular-shaped wall structure.

In some embodiments, the guide containing member may be a removable sleeve or sheath-like member. Typically, the sleeve would be open at both ends and removably placable on the port so that the guides, integrally formed within the sleeve, are substantially adjacent to the tubular-shaped wall of the port.

The sleeve or sheath-like member may be made wholly, or partially, of one or more elastomeric materials or one or more plastic materials.

In some embodiments, the sleeve or sheath-like member may be split along a groove allowing it to expand and be placed on the tubular-shaped portion of ports having different diameters and/or dimensions. The sleeve or sheath-like members discussed above may be considered to be universal guide containing members, suitable for use with a range of ports having different diameters and/or dimensions.

When the attachment structure is made of plastic or elastomeric materials, the structure may be molded to contain as many guides 14 as required. Thread-guide members 16 are insertable into the guides positioned in the guide containing members.

In another embodiment of the present invention (not shown in the figures), outer side 4a of wall 4 may have a shape other than the preset shape of the wound channel. Its cross section may be shaped as an ellipse, a triangle, etc. In this case it is sensible to insert the proposed device into the wound channel with the help of the guide.

In the Figures provided and discussed above, the thread-guiding members have trajectories which intersect at a point. It should be understood that in other embodiments the thread-guiding members need not intersect at a point, but one trajectory may be projected so that its projection intersects another trajectory. However, as noted above, all that is required of guides 14a and 14b in the present invention is that guides 14a and 14b allow for the trajectories 22 of thread-guiding members 16 to pass through pre-specified points in the body cavity.

The use of the device of the present invention allows reliable preservation of the initial shape of the wound channel and of the stable layer structure of the wound, as well as the possibility of making a strictly directed suture. This considerably reduces the disarrangement of approximation of layers of the abdominal or thoracic wall, and, hence, diminishes the risk of post-surgical complications such as bleeding, suppuration and hernias. Additionally, the use of the proposed device eliminates the time-consuming step of searching for the wound channel after the port is removed. This facilitates considerably wound suturing after an operation. The device of the present invention may also be used to fix various tissues and materials inside the abdominal, the thoracic or other cavity.

Figure 6A:
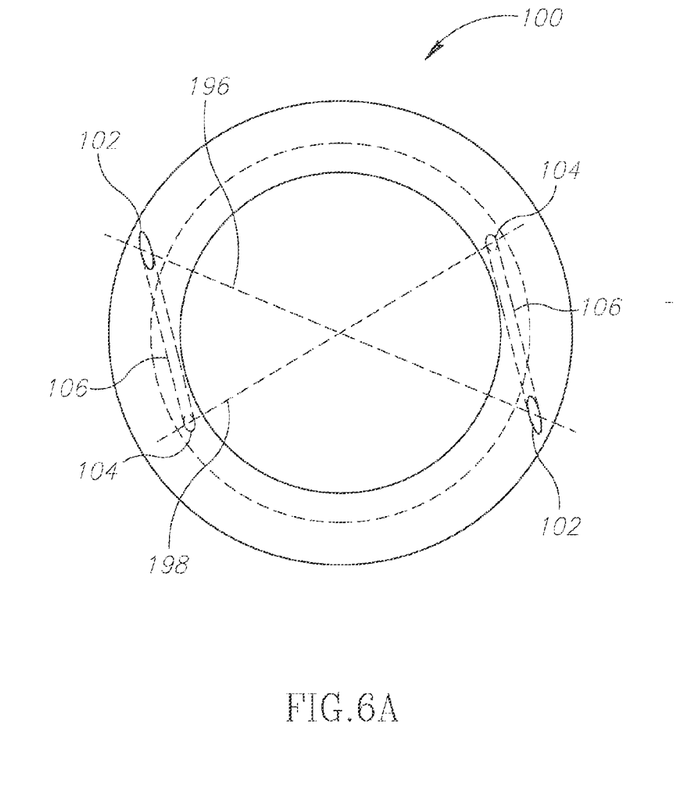
FIGS. 6A and 6B are top and perspective views of a ring device for guiding needles when suturing.
Figure 6B:
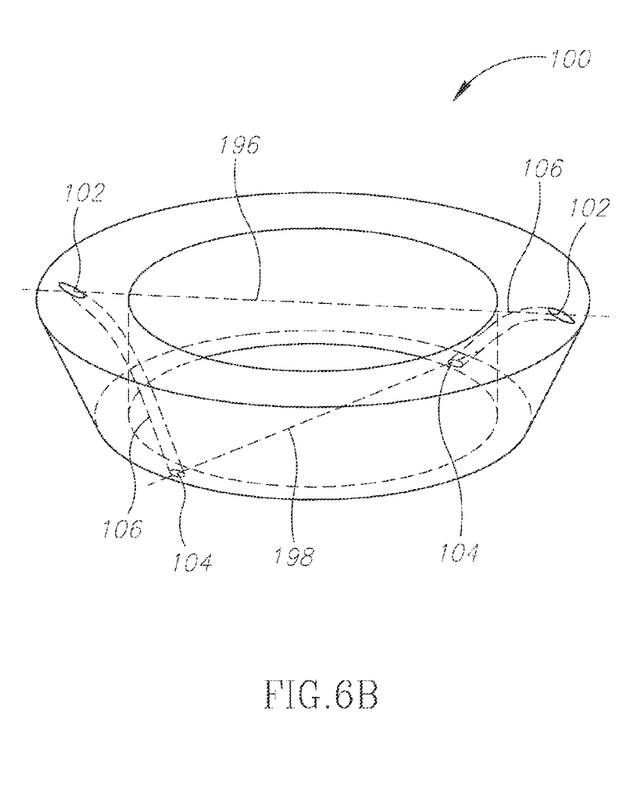
Figure 6C:
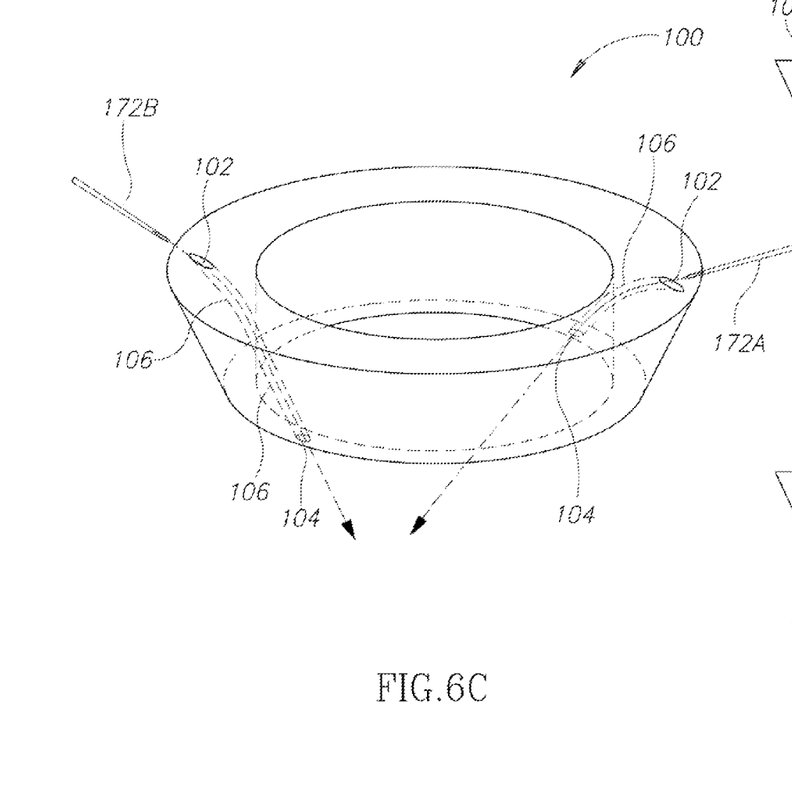
FIG. 6C is a perspective view of the ring device in FIGS. 6A and 6B showing the entry and exit of two needles from the channels in the ring device.

Turning now to new embodiments of the present invention, reference is made to FIGS. 6A through 6E. FIGS. 6A and 6B show a top and a perspective view, respectively, of a ring device 100 provided by the present invention. Both views show entry holes 102 of guide channels 106 and exit holes 104. The entry 102 and exit 104 holes are both often denoted as guide holes, individually or in combination. The entry holes 102 are positioned on the top surface of ring shaped device 100 while exit holes 104 are on the bottom surface of the device. Guide channels 106 connect entry 102 and exit holes 104 and channels 106 are partially curved near entry holes 102 as can be seen in the Figures. FIG. 6C also shows a perspective view of ring device 100 with flexible needles 172A and 172B shown entering into channels 106 and their direction of exit therefrom. Typically, the needles are flexible hollow needles and a suture is positioned within the hollow of the needles. The channels in FIGS. 6A-6E clearly show that the channels are curved in the region of their entry holes. The straight portion of channels 106 are typically about 50% to about 75% of the entire length of channels 106, This straight portion constitutes the part of channels 106 beginning at and proceeding from exit holes 104 in the direction of entry holes 102. FIG. 6C clearly shows the direction and the angle of entry of needles 172A and 172B. It shows that the angle of entry of needles 172A and 172B into entry holes 102 is an acute angle with reference to the top surface of device 100. The angle of entry is less than 30 degrees, often less than 20 degrees. FIG. 6A, in conjunction with FIGS. 6B and 6C (and FIGS. 7A and 8A-10B discussed below), show that the channels 106 extend in opposite directions from each other along their entire length when proceeding along said channels. The needles progress in opposite directions as they advance from their respective entry holes 102 to their respective exit holes 104. As readily seen in FIG. 6A, one channel extends from the bottom of the page to the top while the other extends from the top to the bottom of the page when the reader faces the page.

While device 100 is described as a ring or ring-shaped herein, as is split ring device 130 discussed below, it more accurately may be described as a frustum of a hollow right circular cone. The smaller end of the frustum is, during use, positioned adjacent to the body wall of the patient on whom suturing is to take place. With that understanding, the term ring or ring-shaped will continue to be used for the frustum-shaped devices discussed herein.

Figure 6D:
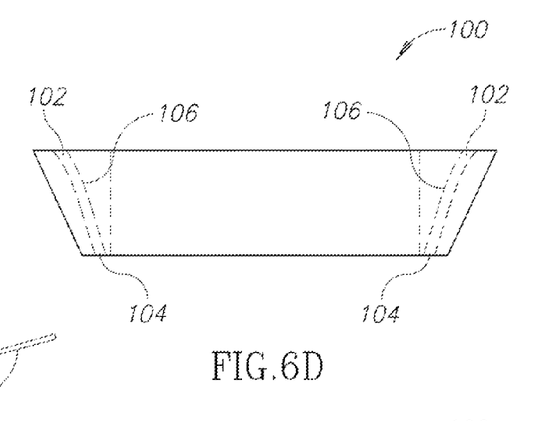
FIGS. 6D and 6E are two side views of the ring device in FIGS. 6A and 6B.
Figure 6E:
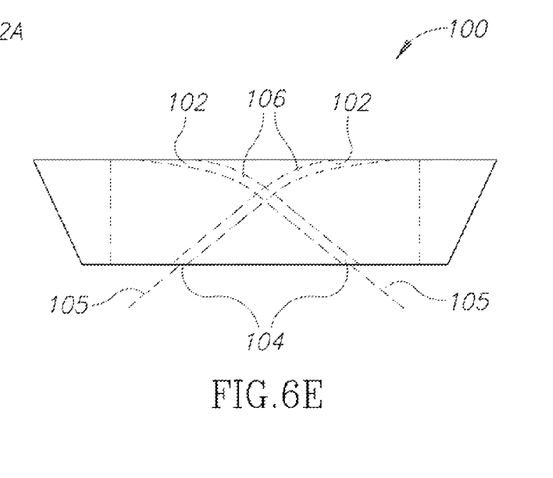

FIGS. 6D and 6E, to which reference is now made, show two side views of device 100. These views clearly show the curved configurations and orientation of guide channels 106 with respect to the device and with respect to each other. The curved configuration and orientation of channels 106 will be discussed further below.

FIGS. 6D and 6E also clearly show the frustum shape of device 100. They also show the exit axis 105 of each guide channel 106. The exit axis 105 is equivalent to the portion of the central axis of the guide channels as it approaches exit holes 104 and passes out of channel 106.

Figure 7A:
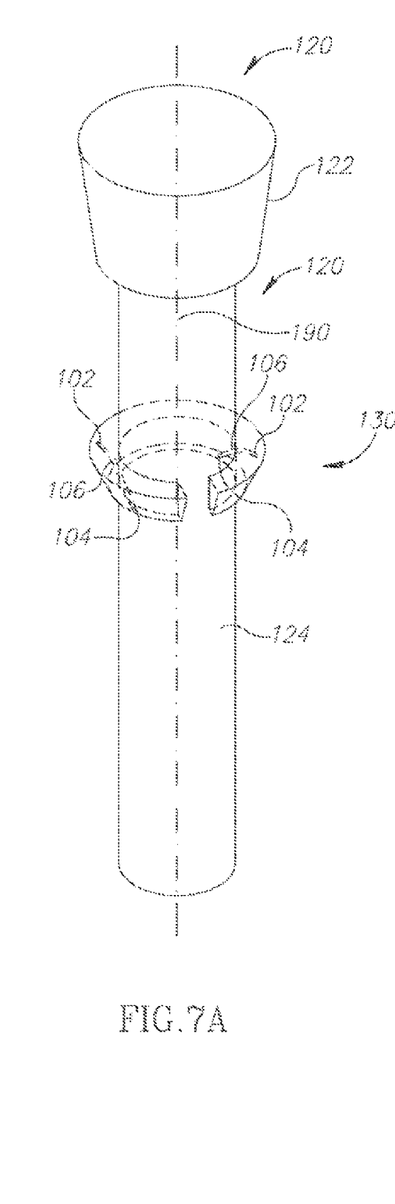
FIG. 7A is a side view of a split ring device encompassing the body of a trocar.
Figure 7B:
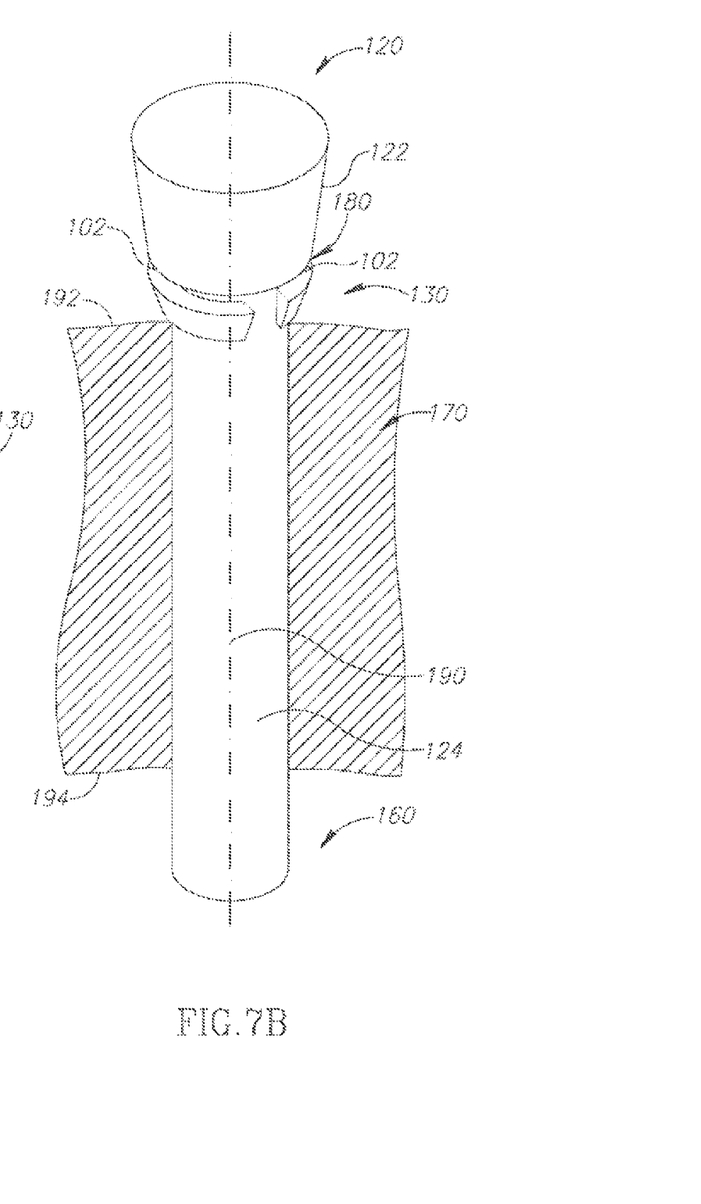
FIG. 7B is a side view of a split ring device encompassing the body of a trocar when, for example, the patient is obese.

Reference is now made to FIGS. 7A and 7B where the ring device shown is a split ring device 130 for guiding flexible needles. Device 130 is positioned on the body 124 of trocar 120 as when in use. In FIG.7A, entry holes 102 and exit holes 104 are shown as are curved channels 106. Entry 102 and exit hole 104, as well as curved channels 106 of device 130, are positioned 180 degrees from each other. The two entry holes 102 form a first straight line 196 (FIG. 6B) passing through the longitudinal axis 190 of trocar 120 and perpendicular to it. Similarly, the two exit holes 104 of the device form a second straight line 198 (FIG. 6B) passing through the longitudinal axis 190 of trocar 120 and perpendicular to it. One curved channel 106 shown extends away from its entry hole, while the second channel 106 extends away from its entry hole in the opposite direction.

FIG. 7B shows the position of split ring device 130 positioned on trocar 120 with the trocar extending through body wall 170. During use, particularly when the patient is obese, the trocar body 124 must pass through a significant amount of fatty tissue before it enters a body cavity 160. For that reason, split ring device 130 is pushed up close to head 122 of trocar 120. The head 122 of trocar 120 with obese patients often must be held down against the body wall 170 to counter the natural tendency of the body to push the trocar 120 out of body cavity 160. Accordingly, split ring device 130 is often positioned close or nearly adjacent to head 122 of trocar 120.

As a matter of orientation in what is described herein, internal refers to the side of the body wall 170 where the body cavity 160 is located, while external is on the side of the body wall 170 distal from the body cavity 160. The external layer of body wall 170 is the skin 192 and the internal layer of body wall 170 is the peritoneum 194.

Generally, there is a gap 180 between split ring device 130 and trocar head 122. However, in many cases, such as with obese patients, this gap 180 is relatively small. The fact that split ring device 130 often is positioned with a small gap 180 between it and head 122 of the trocar means that inserting a flexible needle with its attached suture into a channel 106 of device 130 is difficult. If channels 106 were straight as they are in prior art, it would be very difficult to insert the flexible needles into channels 106 and bring them with their associated sutures through the channels into body cavity 160. Since one hand of the surgeon generally must be used to hold down the trocar 120, inserting the needles into channels 106 with one hand is difficult. However, since channels 106 are curved at, and as they proceed away from, their entry holes 102, inserting flexible needles as in FIG. 6C at an acute angle into channels 106 is much easier. The curved channels often allow single hand insertion of the needle while the trocar head 122 is being pushed in the direction of the body cavity 160 by the surgeon's second hand. The curved section of channels 106 allow for easier entry of needles even when non-obese patients are being treated.

With some current devices and methods, the trocar 120 must be removed before suturing begins causing the surgeon to search essentially blindly for the location of the wound to be sutured. This results in less exact suturing, often necessitates more than two sutures, and generally requires more time, often significantly more time, for the suturing procedure. The present device does not require removal of the trocar prior to suturing.

Figure 10A:
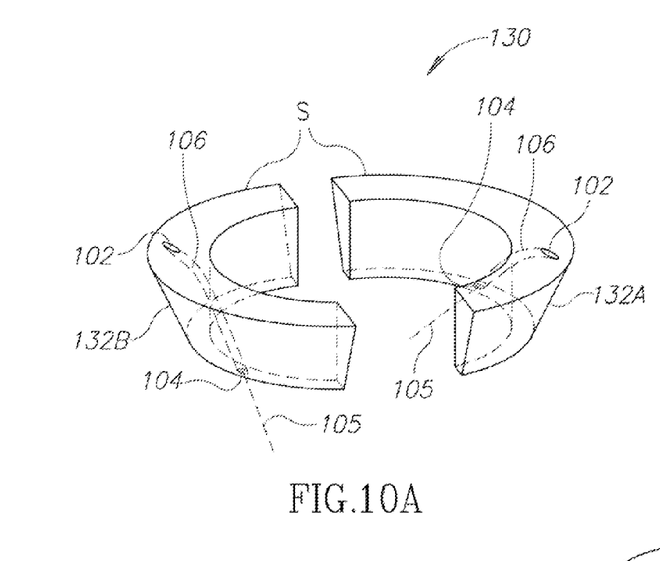
FIGS. 10A-10B are perspective views of the split ring device in their open and closed configurations, respectively.
Figure 10B:
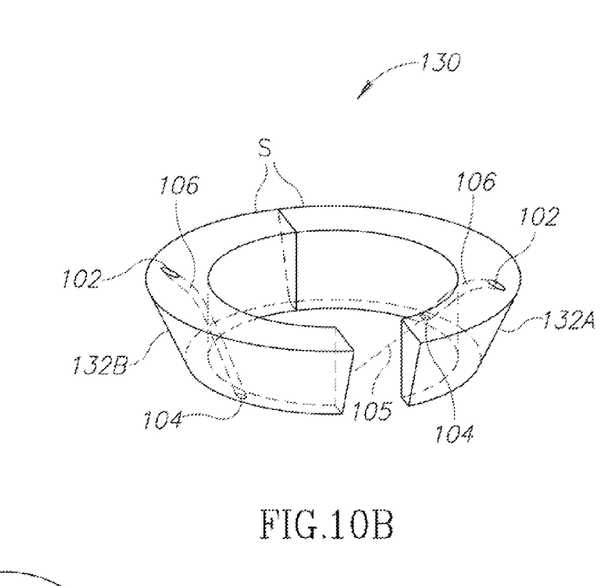

Channels 106 are angled as they approach exit holes 104 as is best seen in FIGS. 10A and 10B for split ring device 130 and FIG. 6E for whole ring device 100. The angle is predetermined, often but without intending to limit the invention, between about 15 and about 30 degrees with respect to the bottom surface of the ring, so that the needles after exiting channels 106 pass through body wall 170, and enter body cavity 160. As the needles enter body cavity 160 the needles are 180 degrees apart and located at about 1-2.5 cm from the nearest point on the body 124 of trocar 120. This provides an essentially predefined location for the sutures that are brought into body cavity 160.

A surgeon using a second trocar through which a grasper is inserted into the body cavity pulls the sutures provided by needles 172A and 172B using device 100 or 130 positioned on first trocar 120. The sutures are pulled by the grasper outside the body cavity 160 and tied. Because of the structures of devices 100 or 130, the sutures are delivered to a predefined area in the body cavity, and the surgeon can locate the sutures without searching for the needles as is the case when other prior art devices or methods are used. This is true even with obese patients. Understandably, such searching is often difficult when the area the sutures are to be found in is insufficiently localized before hand and is made even more difficult if excessive bleeding occurs.

Figure 8A:
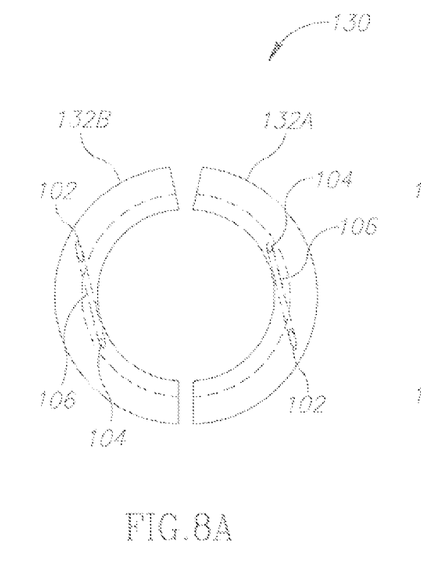
FIGS. 8A-8B are top views of the split ring device in their closed and open configurations, respectively.
Figure 8B:
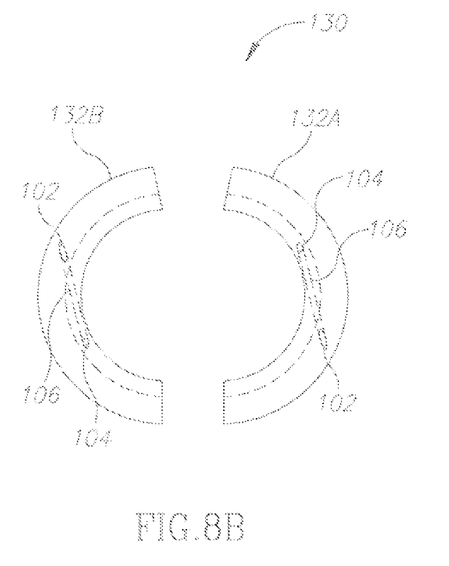

Reference is now made to FIGS. 8A and 8B where top views of split ring device 130 and its two halves 132A and 132B are shown. Entry holes 102 are shown and both in the ring's open (FIG. 8B) and closed configuration (FIG. 8A), the entry holes 102 are 180 degrees apart. Curved channels 106 are shown and from this view it is evident that the channels extend to their respective exit holes 104 but in opposite directions. From this view the curvature of the channels is not seen well but it can be seen better in, for example, FIGS. 10A and 10B discussed below.

Figure 9A:
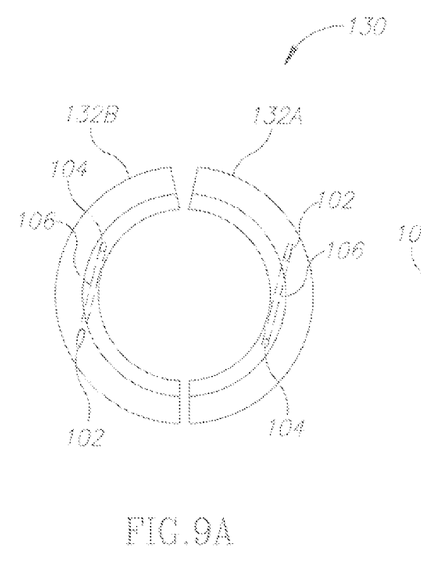
FIGS. 9A-9B are bottom views of the split ring device in their closed and open configurations, respectively.
Figure 9B:
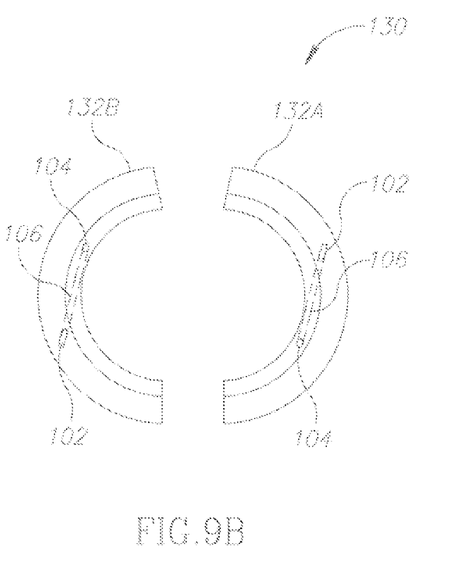

FIGS. 9A and 9B, to which reference is now made, are bottom views of split ring device 130. The two halves 132A and 132B of the split ring are shown in their closed and open configurations, respectively; exit holes 104 are shown as being positioned near the circumference of the split ring, 180 degrees apart. Even when the split ring device 130 is in its open configuration (FIG. 8B) the exit holes 104 remain 180 degrees apart.

It should be noted that the diameter of the channels is sized to contain the flexible needles to be used and the sutures which they carry from entry holes 102 through channels 106, past exit holes 104, through body wall 170 and into body cavity 160. There is a need for a sufficiently snug fit of the needles in the channels 106 so that needles may exit the body wall 170 into body cavity 160 at substantially the predetermined angle. While the diameter of the channels is substantially the same as that of the needles, it is readily evident that the channels' diameter is slightly larger to allow the needles to be advanced through the channels 106 and exit holes 104. However, the diameter of the channels generally is such as to allow transit of the needles while producing a sufficiently snug fit for the reason mentioned above.

FIGS. 10A and 10B show top perspective views of split ring device 130 in its open and closed configurations, respectively. A spring used to transition split ring device 130 from its closed to its open configuration is not shown but is schematically represented by "S". "S" is schematically shown as being joined to both halves 132A and 132B of split ring device 130. The spring may be any of many springs known to persons skilled in the art. The spring is used by the surgeon to separate the halves 132A and 132B of split ring device 130 and the resilient force provided by the spring allows for the split ring device 130 to be held to trocar 120. It should be noted that the views in FIGS. 10A and 10B show the curvature of channels 106.

Figure 11:
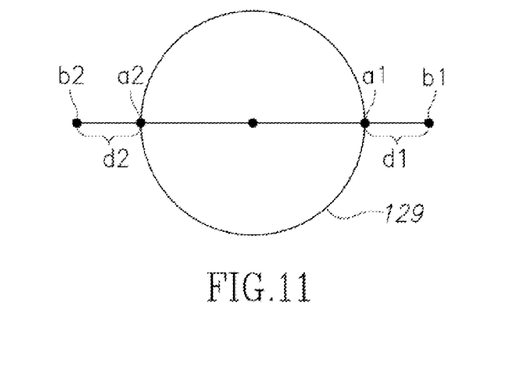
FIG. 11 is a top view of the body of a trocar and its relationship to the points at which needles guided by the devices discussed herein enter the body cavity.

Reference is now made to FIG. 11, which shows the circumference 129 of trocar 120 with two symmetric points a1 and a2 on the circumference. The points b1 and b2 represent the points at which the needles exit the body wall 170 into body cavity 160 after exiting guide channels 106 of split ring device 130. As discussed above, because of the symmetry of the situation distances d1=d2 and are predetermined to be about 1 to about 2.5 cm from the nearest point on the body of the trocar.

It should readily be understood that Figures, such as FIGS. 6D and 6E, shown for complete ring device 100 are mutatis mutandis applicable to split ring device 130 as well.

The devices 100 and 130 shown in FIGS. 6A-10B may be made of metal, such as stainless steel, and rigid plastics.

Although the invention has been described and illustrated with a certain degree of particularity, it is understood that the present disclosure has only been made by way of example, and that various modifications thereof may be resorted to by those skilled in the art without departing from the spirit and scope of the invention, as hereinafter claimed.

What is claimed is:

1. A device for use with a trocar in suturing trocar wounds with flexible needles, the trocar having a longitudinal axis and positionable to extend through a trocar wound in a body wall into a body cavity, said device comprising:
    a ring encompassing the trocar, said ring movably positionable so as to be positioned adjacent to the body wall, said ring being a split ring having a closed configuration and an open configuration, each half of said split ring including a guide channel passing through said split ring and having an entry hole and an exit hole, said guide channels for guiding the needles through the body wall into the body cavity, said entry holes disposed symmetrically on a diameter of said split ring and forming a first line passing through the longitudinal axis of the trocar and said exit holes disposed symmetrically on a diameter of said split ring forming a second line passing through the longitudinal axis of the trocar when said split ring is in both its closed or open configurations, each half of said split ring being in mechanical connection with a spring member that is operable to cause said halves of said split ring to transition from its open to its closed configuration and vice versa, and
    wherein each of said guide channels includes a smoothly curved portion near its entry hole, said smoothly curved portion joined to a straight portion of said each of said guide channels, said straight portion extending from said smoothly curved portion to said exit hole of said each of said guide channels and comprising 50-80% of the length of said each of said guide channels.

2. A device according to claim 1 wherein said smoothly curved portion of each of said channels has a curvature that allows an angle of entry of the needles into said entry holes at an angle of less than 30 degrees.

3. A device according to claim 1 wherein said split ring has a top surface and a bottom surface and said guide channels are angled at a predetermined angle with respect to the bottom surface of said ring so that the flexible needles passing through said exit holes of said channels exit therefrom into the body wall and then the body cavity at said predetermined angle along an exit axis of said channels so that the needles are at a predetermined distance of between 1 and 2.5 cm from the nearest point on the trocar when the needles enter the body cavity, and are symmetrically disposed with respect to the longitudinal axis.

4. A device according to claim 1 wherein said each of said guide channels extend in opposite directions from each other along their entire length when proceeding along said each of said guide channels from their respective entry holes toward their respective exit holes.

5. A device according to claim 1 wherein said split ring has a top surface and a bottom surface and said each of said guide channels are sized to have a diameter larger than the diameter of the flexible needles to be passed therethrough and so that the needles exit the body wall into the body cavity at a predetermined angle defined by said bottom surface of said split ring and said guide channels.

6. A system for suturing trocar wounds which extend through a body wall to a body cavity, the suturing effected with flexible needles, said system comprising:
    a trocar having a mechanically connected head and body and having a longitudinal axis extending through said trocar body, said trocar positionable to extend through the body wall into the body cavity by way of the trocar wound; and
    a ring encompassing said trocar, said ring movably positionable to be positioned adjacent to the body wall, said ring being a split ring having a closed configuration and an open configuration, each half of said split ring including a guide channel having an entry hole and an exit hole, said guide channels for guiding the needles through the body wall into the body cavity, said entry holes disposed symmetrically on a diameter of said split ring and forming a first line passing through the longitudinal axis of said trocar and said exit holes disposed symmetrically on a diameter of said split ring forming a second line passing through the longitudinal axis of said trocar when said split ring is in both its closed and open configurations, each half of said split spring being in mechanical connection with a spring member that is operable to cause said halves of said split ring to transition from its open to its closed configuration and vice versa, and wherein each of said guide channels includes a smoothly curved portion near its entry hole, said smoothly curved portion joined to a straight portion of said each of said guide channels, said straight portion extending from said smoothly curved portion to said exit hole of said each of said guide channels and comprising 50-80% of the length of said each of said guide channels.

7. A system according to claim 6, wherein said smoothly curved portion of each of said channels has a curvature that allows an angle of entry of the needles into said entry holes at an angle of less than 30 degrees.

8. A system according to claim 6 wherein said split ring has a top surface and a bottom surface and said guide channels are angled at a predetermined angle with respect to said bottom surface of said split ring so that the flexible needles passing through said exit holes of said channels exit therefrom into the body wall and then the body cavity at said predetermined angle along an exit axis of said channels so that the needles are at a predetermined distance of between 1 and 2.5 cm from the nearest point on said trocar when the needles enter the body cavity and are symmetrically disposed with respect to the longitudinal axis.

9. A system according to claim 6, wherein said each of said guide channels extend in opposite directions from each other along their entire length when proceeding along said each of said guide channels from their respective entry holes toward their respective exit holes.

10. A system according to claim 6, wherein said split ring has a top surface and a bottom surface and said each of said guide channels are sized to have a diameter larger than the diameter of the flexible needles to be passed therethrough and so that the needles exit the body wall into the body cavity at a predetermined angle defined by said bottom surface of said split ring and said guide 11. A device for use with a trocar in suturing trocar wounds with flexible needles, the trocar having a longitudinal axis and positionable to extend through a trocar wound in a body wall into a body cavity, said device comprising:

a split ring having a closed configuration and an open configuration and encompassing the trocar, said split ring movably positionable so as to be positioned adjacent to the body wall, each half of said split ring including a guide channel having an entry hole and an exit hole passing through said split ring, each half of said split ring being in mechanical connection with a spring member that is operable to cause said halves of said split ring to transition from its open to its closed configuration and vice versa, and wherein each of said guide channels includes a smoothly curved portion near its entry hole, said smoothly curved portion joined to a straight portion of said each of said guide channels, said straight portion extending from said smoothly curved portion to said exit hole of said each of said guide channels.

\* \* \* \* \*